(12) United States Patent
Isaev et al.

(10) Patent No.: US 9,546,188 B2
(45) Date of Patent: Jan. 17, 2017

(54) COMPLEXES OF GERMANIUM WITH AMINO ACIDS AND CARBOXYLIC ACIDS AND METHOD FOR PREPARING SAME

(71) Applicant: OBSCHESTVO S OGRANICHENNOI OTVETSTVENNOSTYU "WDS FARMA", Moscow (RU)

(72) Inventors: Alexandr Dmitrievich Isaev, Moscow (RU); Tamaz Omarovich Manasherov, Moscow (RU); Igor Valerievich Ambrosov, Moscow (RU); Svetlana Konstantinovna Matelo, Mechnikovo (RU)

(73) Assignee: OBSCHESNO S OGRANICHENNOI OTVETSTVENNOSTYU "WDS FARMA", Moscow (RU)

( * ) Notice: Subject to any disclaimer, the term of this patent is extended or adjusted under 35 U.S.C. 154(b) by 118 days.

(21) Appl. No.: 14/372,807

(22) PCT Filed: Nov. 9, 2012

(86) PCT No.: PCT/RU2012/000922
§ 371 (c)(1),
(2) Date: Jul. 17, 2014

(87) PCT Pub. No.: WO2013/112072
PCT Pub. Date: Aug. 1, 2013

(65) Prior Publication Data
US 2015/0011523 A1 Jan. 8, 2015

(30) Foreign Application Priority Data
Jan. 25, 2012 (RU) .............................. 2012102525

(51) Int. Cl.
| C07F 7/30 | (2006.01) |
| A61K 31/555 | (2006.01) |
| A61K 33/24 | (2006.01) |
| C07F 7/00 | (2006.01) |

(52) U.S. Cl.
CPC ............... *C07F 7/30* (2013.01); *A61K 31/555* (2013.01); *A61K 33/24* (2013.01); *C07F 7/003* (2013.01)

(58) Field of Classification Search
CPC ........................................................ C07F 7/30
See application file for complete search history.

(56) References Cited

U.S. PATENT DOCUMENTS

| 3,674,823 A | 7/1972 | Makabe |
| 3,825,546 A | 7/1974 | Rice |
| 4,271,084 A | 6/1981 | Ishikawa et al. |
| 4,281,015 A | 7/1981 | Ishikawa et al. |
| 4,296,123 A | 10/1981 | Ishikawa et al. |
| 4,309,412 A | 1/1982 | Ishikawa et al. |
| 4,321,273 A | 3/1982 | Ishikawa et al. |
| 4,322,402 A | 3/1982 | Ishikawa et al. |
| 4,468,393 A | 8/1984 | Geschickter |
| 4,473,581 A | 9/1984 | Ishida et al. |
| 4,898,882 A | 2/1990 | Nagahama |
| 5,340,806 A | 8/1994 | Sawai et al. |
| 5,386,046 A | 1/1995 | Arnold |

FOREIGN PATENT DOCUMENTS

| CN | 1154359 A | 7/1997 |
| CN | 102160603 A | 8/2011 |
| DE | 32 12 817 AI | 10/1983 |
| DE | 37 30277 A1 | 3/1989 |
| EP | 0 091 114 A1 | 10/1983 |
| JP | 48-19496 A | 3/1973 |
| JP | 48 96523 A | 10/1973 |
| JP | 2001-139587 A | 6/1989 |
| RU | 2 171 259 C2 | 7/2001 |
| UA | 65 589 C2 | 12/2011 |

OTHER PUBLICATIONS

Lavayssiere et al. CAS Accession No. 1977:584626.*
English Abstract of UA 65 589 C2 published Dec. 12, 2011.
English Abstract of JP 2001-139587 A published Jun. 1, 1989.
English Abstract of RU 2 171 259 C2 published Jul. 27, 2001.
Office Action dated Jan. 28, 2015 for EP Application No. 12866873.8.
Office Action dated Jul. 17, 2015 for Australian Application No. 2012367370.
Office Action dated Sep. 29, 2015 for Chinese Application No. 201280071062.0.
Office Action dated Oct. 14, 2015 for Canadian Application No. 2,862,186.
Office Action dated Dec. 31, 2105 for EP Application No. 12866873.8.
Office Action dated Jan. 26, 2016 for Korean Application 10-2014-7023604.
espacenet English abstract of CN 1154359 A.
espacenet English abstract of CN 102160603 A.
espacenet English abstract of EP 0 091 114 A1.
Martsinko, E.E., et al., "Synthesis and Study of Co(II), Ni(II), and Cu(II) Ethylenediaminetetraacetatohydroxogermanates", Russian J. of Coordination Chemistry, vol. 31, No. 11, 2005, pp. 796-799.
Lavayssiere, H., et al., "Heterocycles du germanium, du phosphore (III), de L'arsenic-(III) et du soufre a ligand aminoacide ou hydroxyacide", J. Organometallic Chemistry, 137, 1977, pp. C37-C42.
Shestopalov, M.A., et al., "A New Germanium Complex Containing Chelating Pyridinecarboxylate Ligands: cis-Oihydroxybis(pyridine-2-carboxylato-$_k$N$^1$ $_,k$O$^2$) germanium Hydrate (1:2) (cis-[Ge(pyca)$_2$(OH)$_2$] 2 H$_2$O)", Helvetica Chimica Acta, vol. 94, 2011, pp. 1786-1791.
Konopik, N., et al., "Complex compounds of germanic acid with EOTA and EOTA-analogs. II. 1 ,2-0iaminopropane-N,N,N',N'-tetraacetic acid and N-(2-Hydroxyethyl)-1,2- diaminoethane-N,N',N'-triacetic acid", Monatshefte fur Chernie, 100, 1969, pp. 649-663.

* cited by examiner

Primary Examiner — Joseph Kosack
(74) Attorney, Agent, or Firm — Ladas & Parry LLP

(57) ABSTRACT

The invention relates to complexes of germanium with amino acids and carboxylic acids of the general formula Ge[OH]$_a$[AA]$_b$[CA]$_c$ (I), where AA is an amino acid, CA is a carboxylic acid, a=0÷3, b=1÷3, c=0÷3, and 1≤b+c≤4, wherein AA and AC in the complex can be identical or different, and to a method for preparing same. The method consists in preparing an aqueous suspension of germanium dioxide, adding an amino acid and a carboxylic acid to the aqueous suspension of germanium oxide produced, heating the mixture produced with agitation at a temperature of 40-100° C. for 2-14 hours with subsequent filtering, removal of the water and production of a complex in solid form. The method makes it possible to prepare stable complexes with a controllable composition and a controllable ratio of germanium to amino acid and carboxylic acid which are stable in solid form and can be used in medicine.

16 Claims, 11 Drawing Sheets

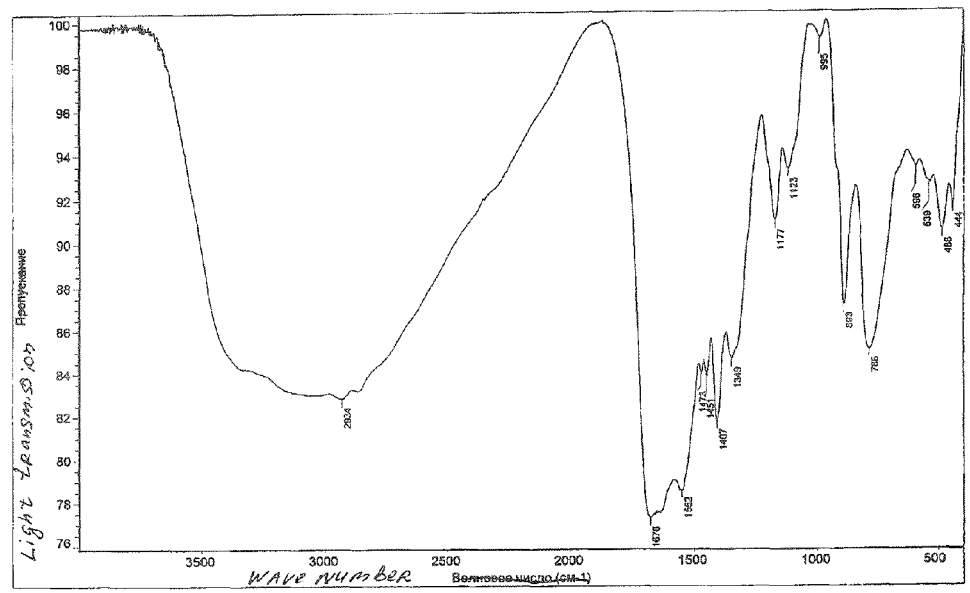
Fig. 1a. IR spectrum for a germanium complex compound with arginine
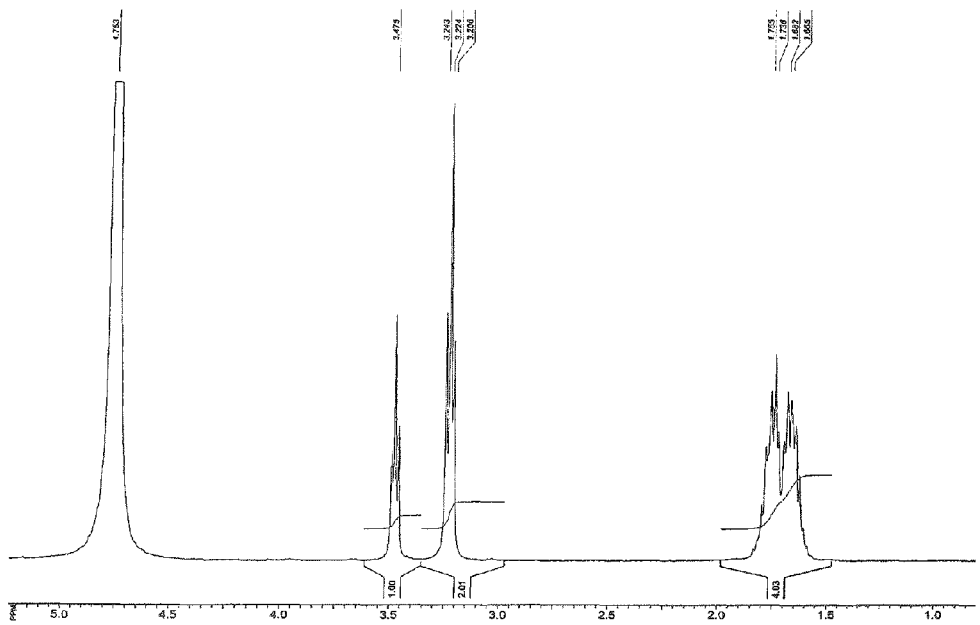
Fig. 1b. $^1$H NMR spectrum in $D_2O$ for a germanium complex compound with arginine

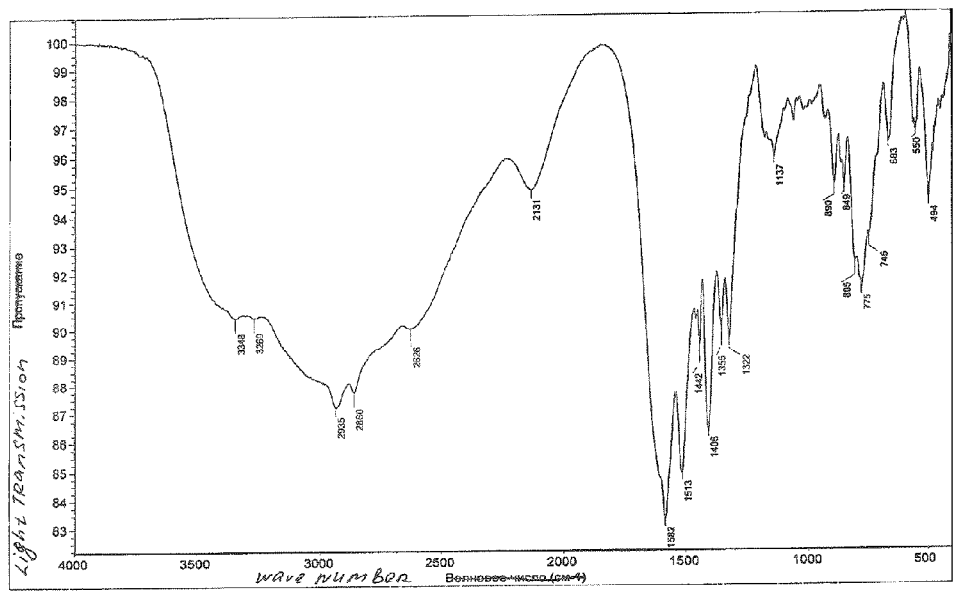
Fig. 2a. IR spectrum for a germanium complex compound with lysine
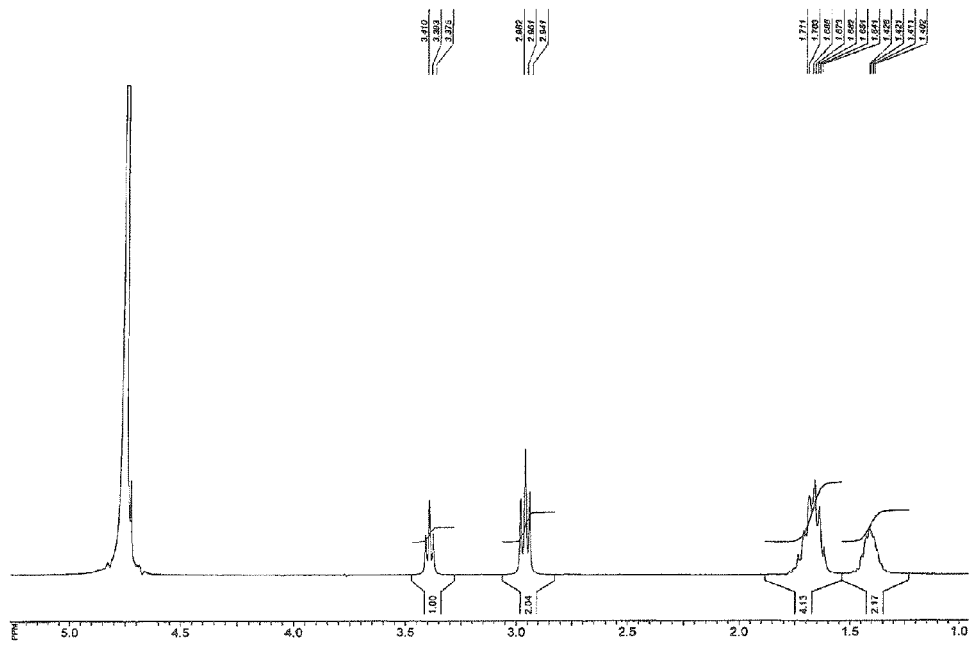
Fig. 2b. $^1$H NMR spectrum in D$_2$O for a germanium complex compound with lysine

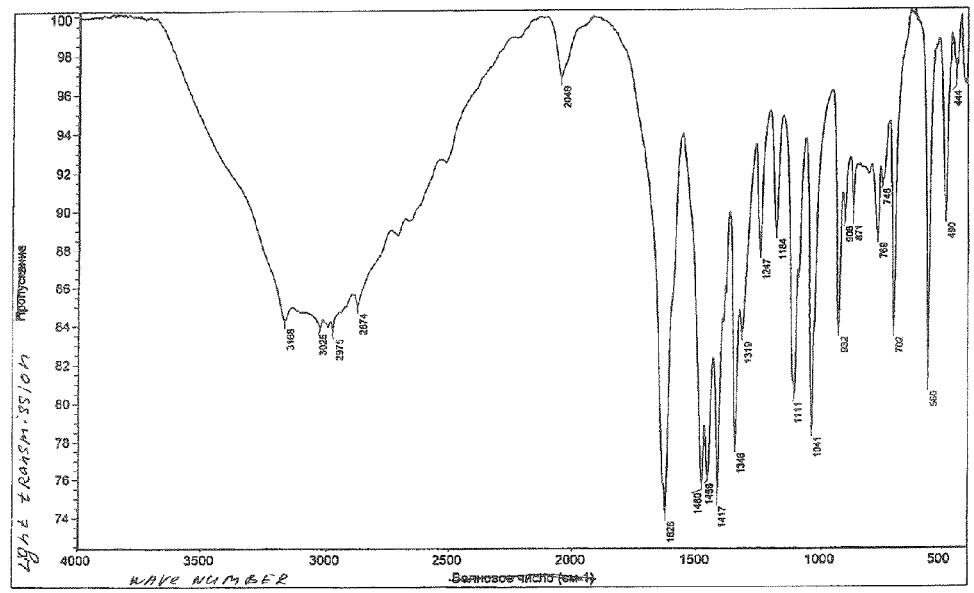
Fig. 3a. IR spectrum for a germanium complex compound with threonine
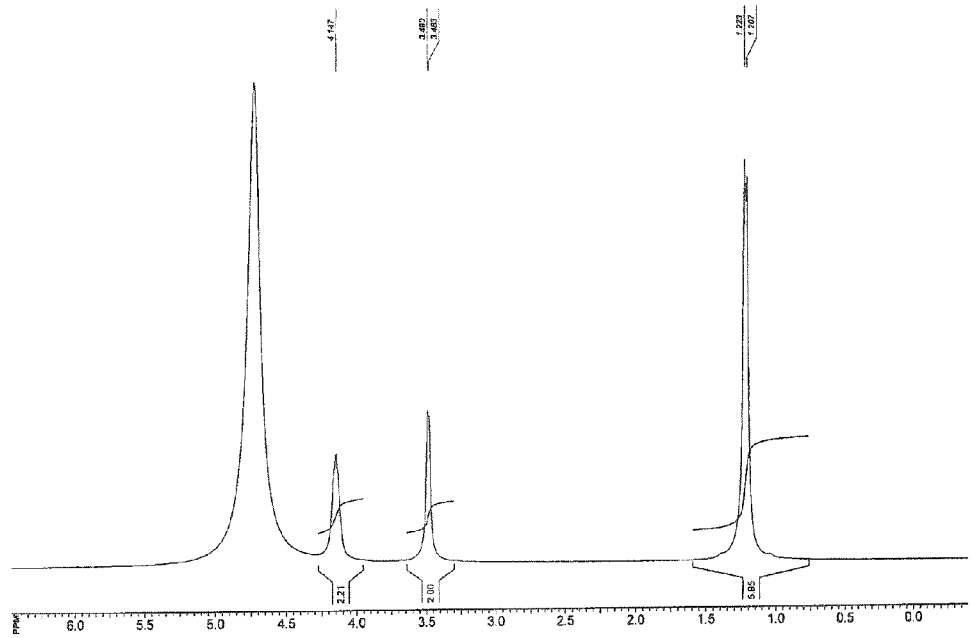
Fig. 3b. $^1$H NMR spectrum in $D_2O$ for a germanium complex compound with threonine

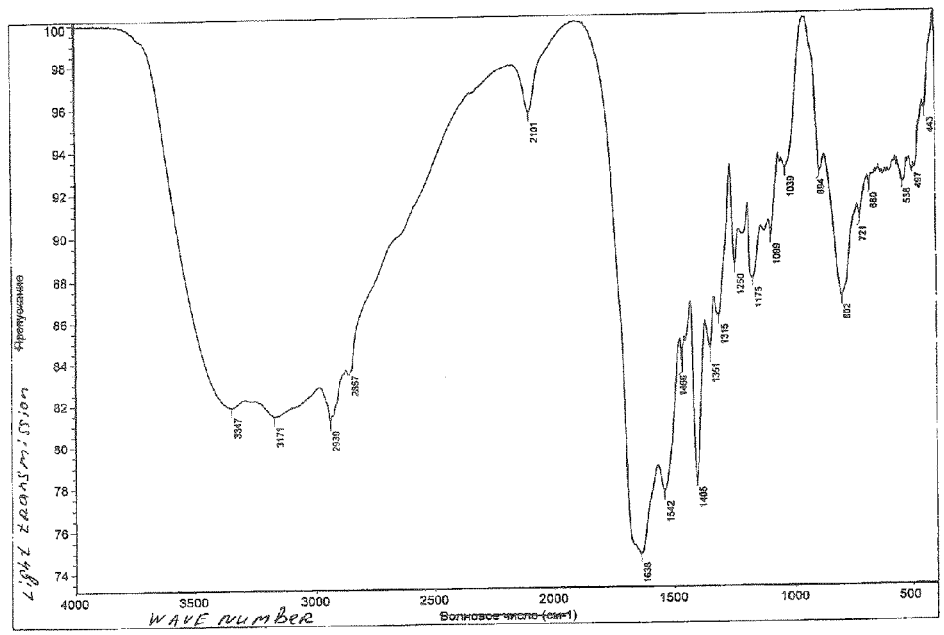
Fig. 4a. IR spectrum for a germanium complex compound with arginine and azelaic acid
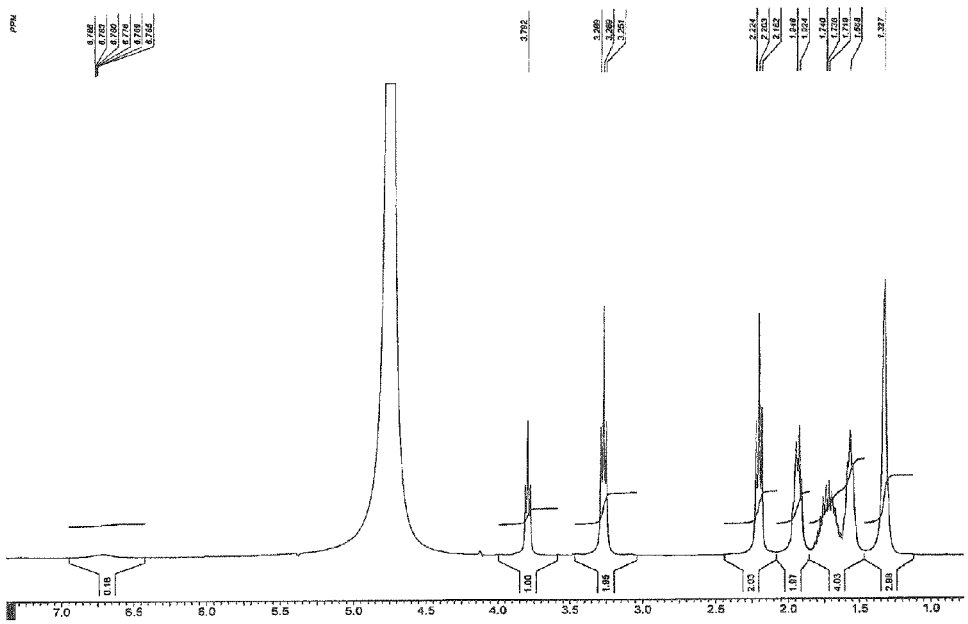
Fig. 4b. $^1$H NMR spectrum in $D_2O$ for a germanium complex compound with arginine and azelaic acid.

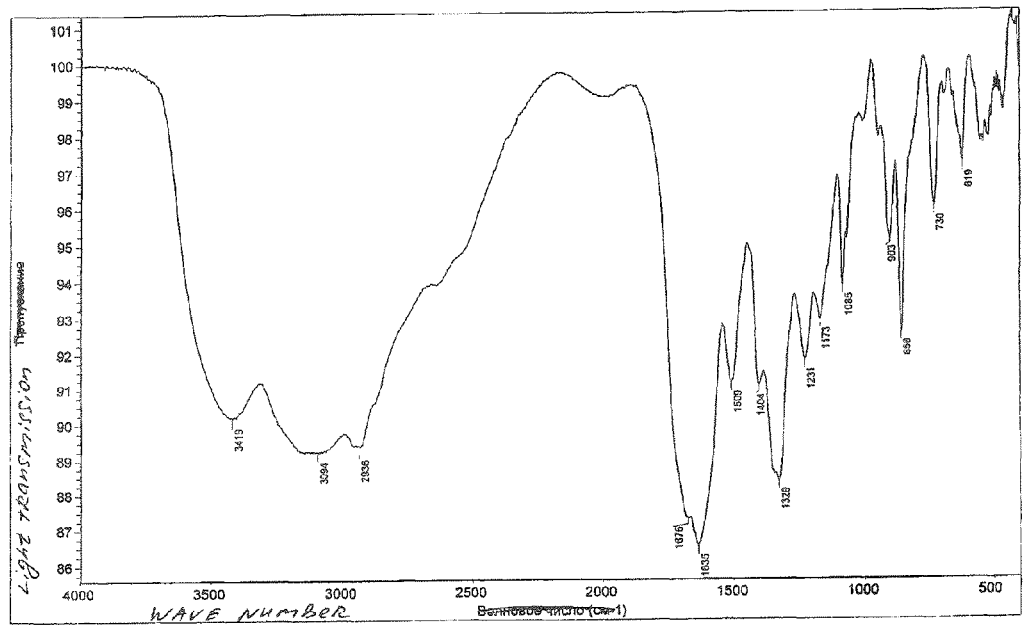
Fig. 5a. IR spectrum for a germanium complex compound with lysine and citric acid
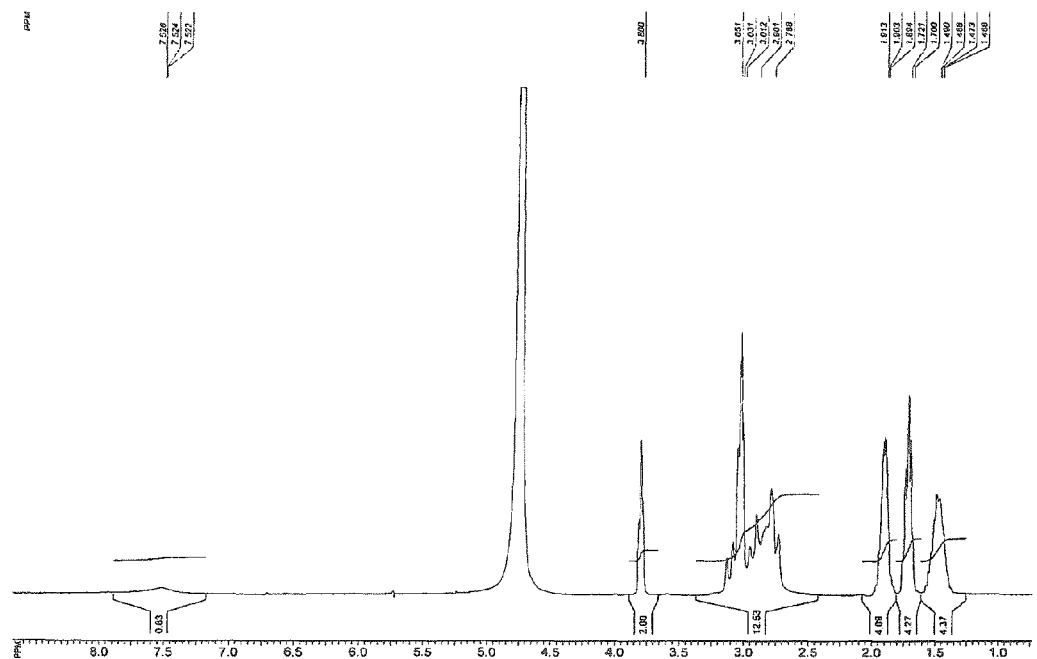
Fig. 5b. $^1$H NMR spectrum in $D_2O$ for a germanium complex compound with lysine and citric acid

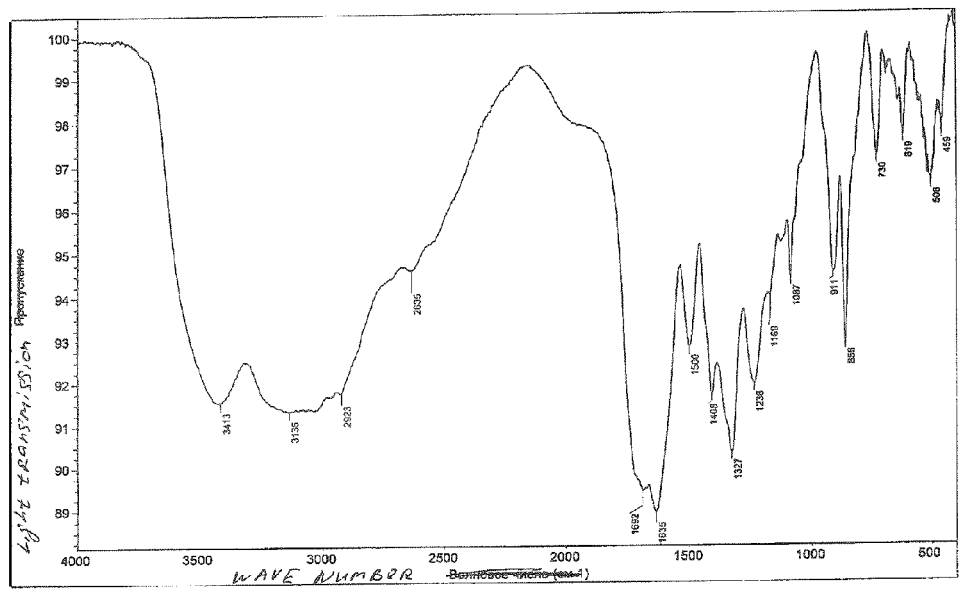
Fig. 6a. IR spectrum for a germanium complex compound with glycine and citric acid
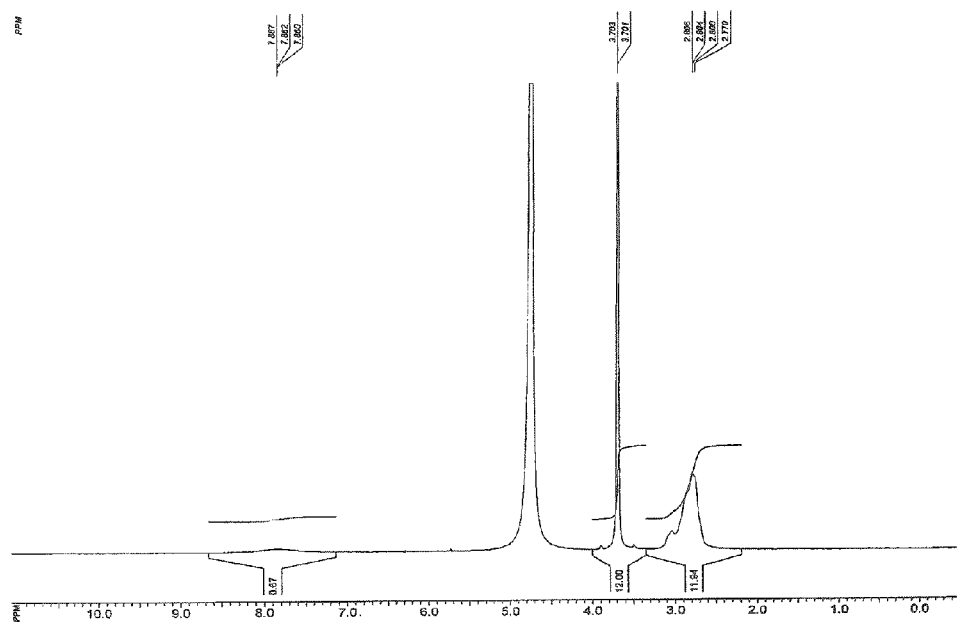
Fig. 6b. $^1$H NMR spectrum in $D_2O$ for a germanium complex compound with glycine and citric acid

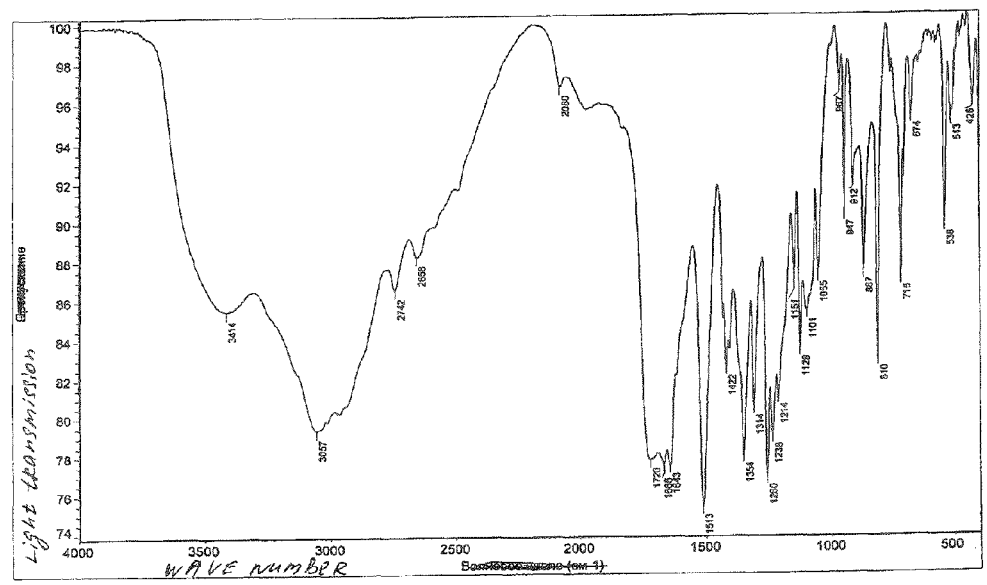
Fig. 7a. IR spectrum for a germanium complex compound with glutamic acid and malic acid
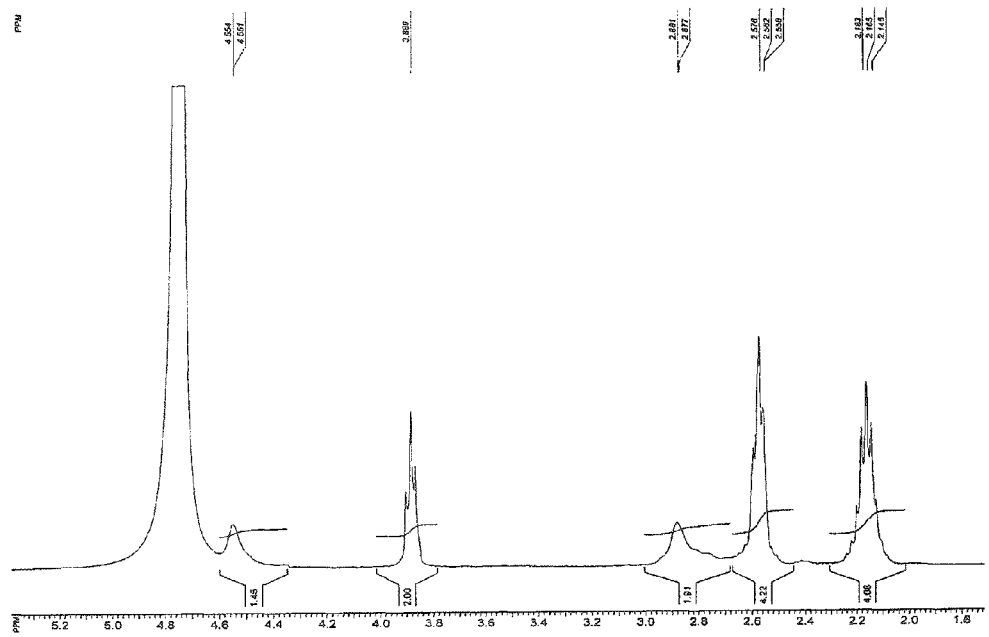
Fig. 7b. $^1$H NMR spectrum in $D_2O$ for a germanium complex compound with glutamic acid and malic acid

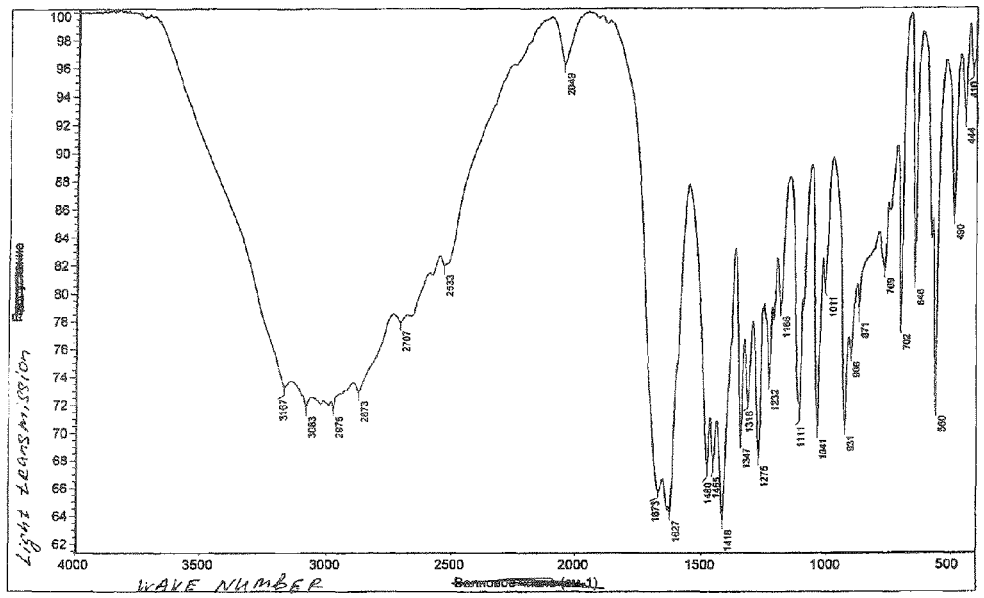
Fig. 8a. IR spectrum for a germanium complex compound with threonine and fumaric acid
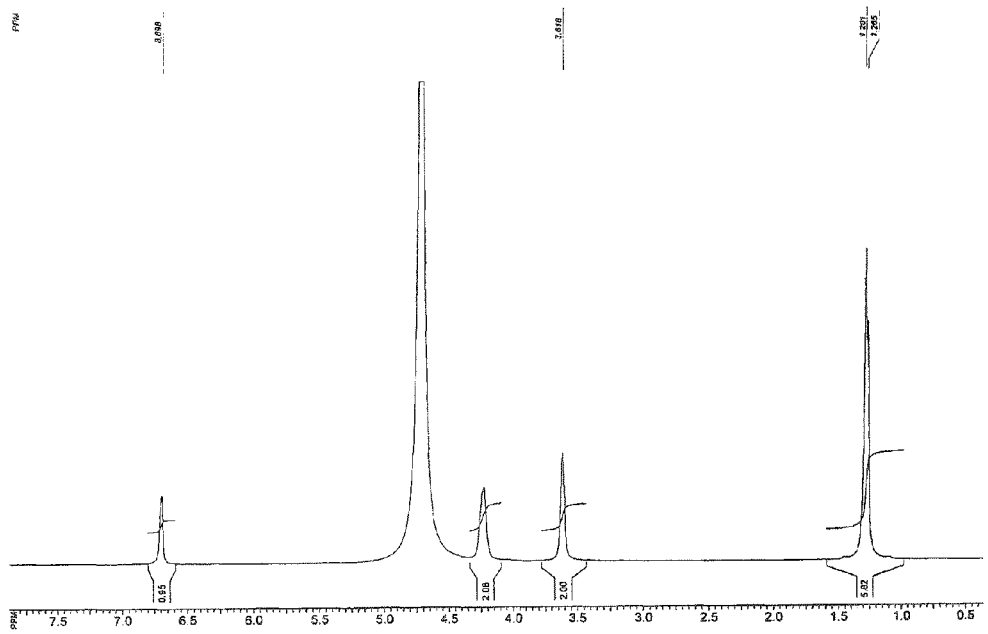
Fig. 8b. $^1$H NMR spectrum in $D_2O$ for a germanium complex compound with threonine and fumaric acid

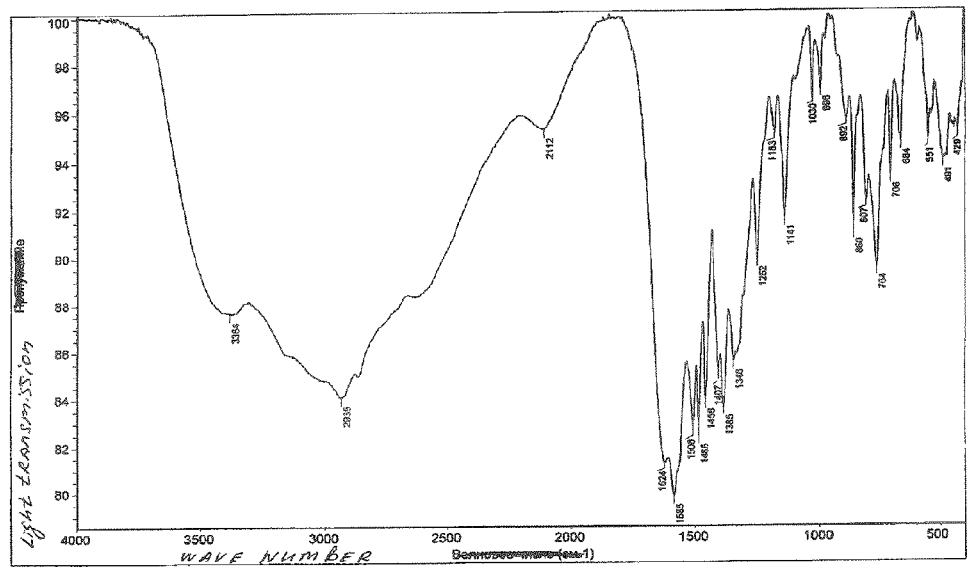
Fig. 9a. IR spectrum for a germanium complex compound with lysine and salicylic acid
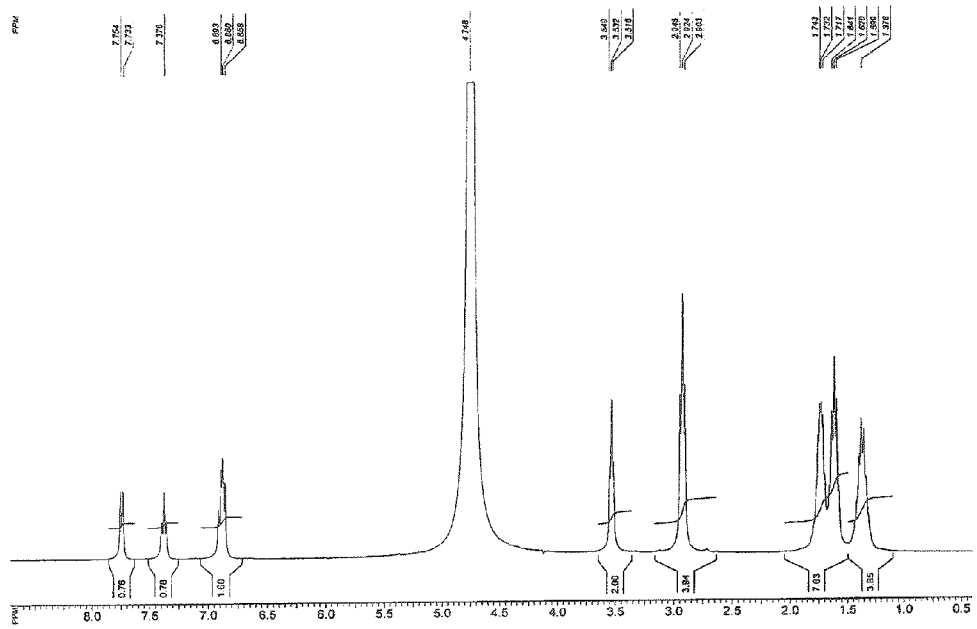
Fig. 9b. $^1$H NMR spectrum in $D_2O$ for a germanium complex compound with lysine and salicylic acid

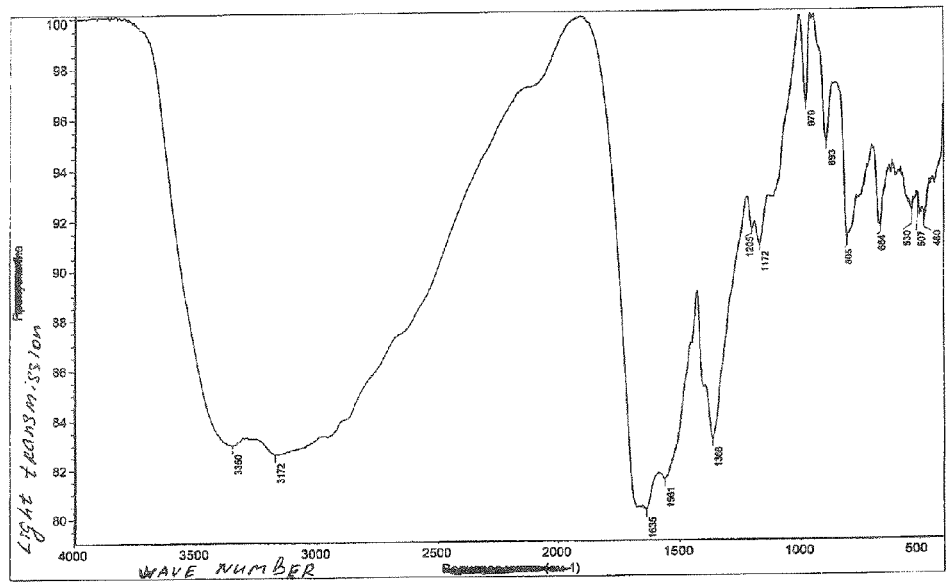
Fig. 10a. IR spectrum for a germanium complex compound with arginine and fumaric acid
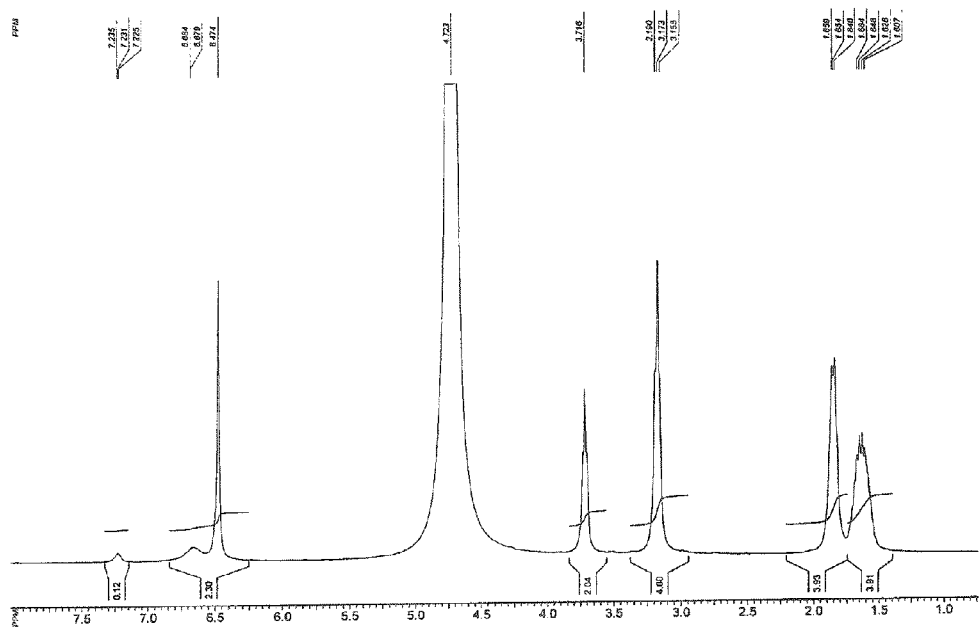
Fig. 10b. $^1$H NMR spectrum in $D_2O$ for a germanium complex compound with arginine and fumaric acid

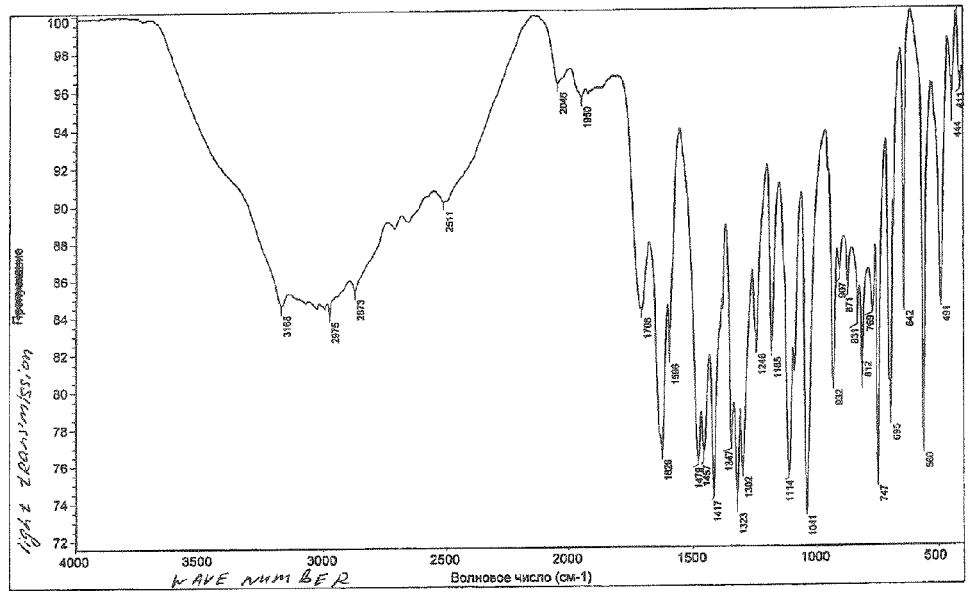
Fig. 11a. IR spectrum for a germanium complex compound with threonine and nicotinic acid
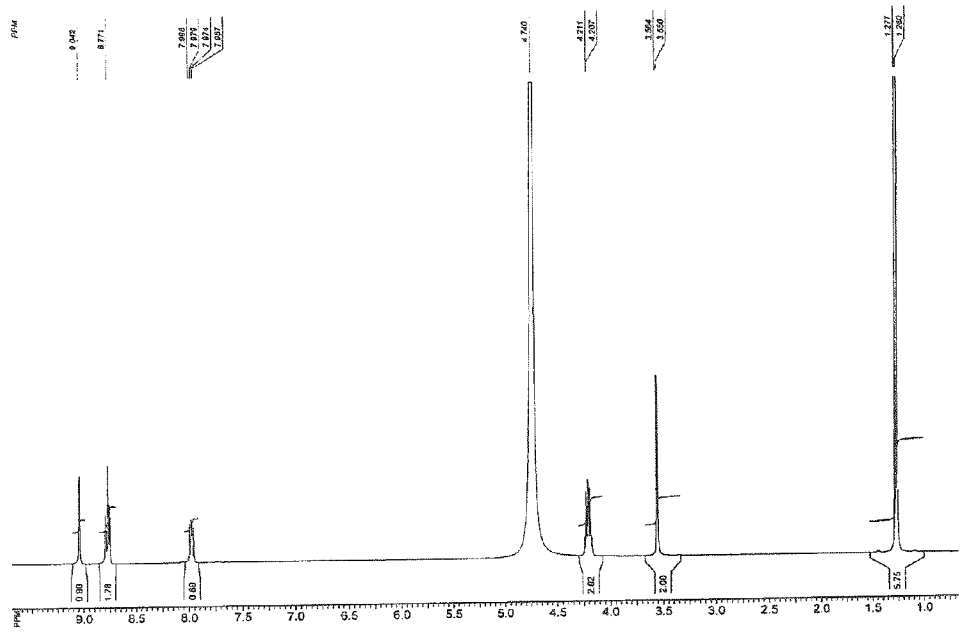
Fig. 11b. $^1$H NMR spectrum in $D_2O$ for a germanium complex compound with threonine and nicotinic acid

COMPLEXES OF GERMANIUM WITH AMINO ACIDS AND CARBOXYLIC ACIDS AND METHOD FOR PREPARING SAME

RELATED APPLICATION INFORMATION

This application is a 371 of International Application PCT/RU2012/000922 filed 9 Nov. 2012 entitled "Complexes Of Germanium With Amino Acids And Carboxylic Acids And Method For Preparing Same", which was published on 1 Aug. 2013 with International Publication Number WO2013/112072 A1, and which claims priority from Russian Patent Application No.: 2012102525 filed 25 Jan. 2012, the content of which is incorporated herein by reference.

THE FIELD OF THE INVENTION

This invention relates to new germanium complex compounds with amino acids and carboxylic acids, and to a method for preparing them.

More particularly, the invention is concerned with the preparation of germanium complex compounds with amino acids and carboxylic acids of general formula (I)

$$Ge[OH]_a[AA]_b[CA]_c \qquad (I)$$

comprising reacting an aqueous solution of a amino acid or a mixture of an amino acid and a carboxylic acid with germanium dioxide. The thus-produced germanium complex compounds can be used in diverse fields of engineering, preferably in medicine.

THE BACKGROUND ART

Germanium-containing compounds are widely used in diverse fields of science and engineering, for example as semiconductors and catalysts for the production of polyesters and polyolefins, in manufacturing optical fibers for telecommunication facilities and lenses and glasses for IR spectroscopy.

Recently germanium compounds have also come into use in medicine due to their pharmacological activities. The biological properties of germanium compounds include the ability to ensure oxygen transport in tissues of the body and to enhance the immune status of the body, and anti-tumor activities.

Germanium compounds are used in two main forms, namely in an organic form (containing Ge—C bonds) or in an inorganic form (as salts, germanium oxides, and complex compounds thereof). For example, U.S. Pat. No. 4,271,084 (1981, IPC: C 07F 7/30) protects germanium-containing organic polymers, namely carboxyethyl germanium sesquioxides, which are produced by the polymerization of 3-trichlorogermylpropionic acid. The feedstock is germanium dioxide, which is reduced with hypophosphorous acid ($H_3PO_2$) in the presence of hydrochloric acid, whereby producing a germanium chloride-phosphoric acid complex. The thus-produced complex compound is converted to 3-trichlorogermylpropionic acid by reaction with acrylic acid ($CH_2=CHCOOH$). The U.S. Pat. No. 5,386,046 (1995, IPC: C07F 7/30) discloses carboxyethyl germanium sesquioxides, which are produced using germanium tetrachloride, tetramethyldisiloxane, and acrylic acid. The prior-art germanium-containing organic polymers are efficient in the treatment of neuropsychiatric disorders (see U.S. Pat. No. 4,281,015, 1981, IPC: A61K 31/28), ophthalmic disorders (see U.S. Pat. No. 4,296,123, 1981, IPC: A61K 31/28), disorders of the liver (see U.S. Pat. No. 4,309,412, 1982, IPC: A61K 31/74), lung fibrosis (see U.S. Pat. No. 4,321,273, 1982, IPC: A61K 31/28), allergic diseases (see U.S. Pat. No. 4,322,402, 1982, IPC: A61K 31/74), and hepatitis (see U.S. Pat. No. 5,340,806, 1994, IPC: A61K 31/79). They also promote the production of interferon in the human body (see U.S. Pat. No. 4,473,581, 1984, IPC: A61K 31/28) and protect it from the cold (see U.S. Pat. No. 4,898,882, 1990, IPC: A61K 31/28).

The U.S. Pat. No. 3,825,546 (1974, IPC: C07D 29/28) describes the preparation of germanium-containing azaspirans (nitrogen-containing heterocyclic compounds), referred to as spirogermaniums. The process of producing spirogermanium is a multi-step synthesis, wherein the initial compound is dialkylgermanium, namely dimethyl- or diethyl-germanium ($R_2GeH_2$). Dialkylgermanium is transformed into 4,4-dialkyl-4-germa-cyclohexanone in two steps using methyl acrylate, potassium tert-butoxide, and 20% sulfuric acid solution. Following this, spirogermanium is obtained from 4,4-dialkyl-4-germa-cyclohexanone in several steps.

The U.S. Pat. No. 4,468,393 (1984, IPC: A61K 31/555) shows that spirogermanium compounds, especially diethyl-spirogermanium and salts thereof, are useful for the treatment of arthritis by means of injections or oral administration. Intravenous injection doses of spirogermanium are between 50 and 80 mg/m² body surface. The therapeutic dose of spirogermanium recommended for treating arthritis with severe rheumatoid symptoms is 1.5 mL aqueous solution (30 mg/mL) intramuscularly. This therapy is to be carried out twice a week during the first six weeks and once a week after remission is achieved. This usually takes a period of three to six months. Oral treatment can be efficient when capsules containing 200 mg spirogermanium are administered twice daily for two weeks and then once daily for six weeks.

The above-described methods for the preparation of germanium-containing organic compounds are multistep and intricate processes. They require that organic solvents be used to isolate and purify target compounds. For example, hydrolysis and condensation of 3-trichlorogermylpropionic acid depend on the process duration and other factors, and this affect the qualities of the final product. The synthesis of spirogermanium comprises five steps, as a result of which the final product yield based on the initial compounds is very low.

Processes are also known for preparing germanium-containing organic compounds that are the products of reacting germanic acid or an alkali-metal salt of metagermanic acid with some amino acids or organic acids. For example, U.S. Pat. No. 3,674,823 (1972, IPC: C07F 7/00) proposes an invention which relates exclusively to a compound of germanic acid and cysteine in the molar ratio 1:1. This compound is active in the treatment of hepatitis, rheumatism, and hydro eczema. The compound is prepared by dissolving a water-soluble form of germanium dioxide in hot water thereby forming germanic acid, then filtering the solution, adjusting pH to 4, and adding cysteine to the aqueous solution of germanic acid. Following this, the solution is heated for 2 hours, then filtered and concentrated by distillation. The product is isolated from the concentrated solution upon cooling. The product can also been isolated by adding ethanol or acetone to the solution. U.S. Pat. No. 3,674,823 does not disclose the feasibility to obtain germanium compounds with other amino acids.

The process for the preparation of germanium compounds that are the product of reacting a potassium or sodium salt of metagermanic acid with some carboxylic acids or amino acids, as disclosed in the patent DE 3212817, 1983, IPC: C07F 7/30, constitutes the most pertinent piece of prior art for our claimed method, and we take it as such. The method for the preparation of germanium compounds as disclosed in the patent DE 3212817 consists in heating germanium oxide with a concentrated aqueous solution of potassium or sodium hydroxide so as to convert the germanium dioxide into a soluble potassium or sodium salt of metagermanic acid; concentrating, cooling, and then suspending the mixture in water under heating with a carboxylic acid, a mixture of carboxylic acids, or an amino acid. The product is obtained in the form of a ready-for-use solution, or is precipitated from the solution by adding an alcohol. Useful amino acids are such as aspartic acid and glutamic acid; useful carboxylic acids include citric acid, isocitric acid, succinic acid, ketoglutaric acid, and fumaric acid; hydroxycarboxylic acids (lactic acid or ascorbic acid) can also be used. The resulting compounds, which are the product of reaction between an alkali-metal salt of metagermanic acid and the aforementioned acids and amino acids, are well soluble in water and have biological and pharmacological properties.

In the patent DE 3212817, the toxicity of germanium compounds with succinic acid and citric acid was studied in mice by the Litchfield and Wilcockson method. For intraperitoneal administration, LD50 was 275 mg/kg and >2 500 mg/kg, respectively. The above-described compounds were subjected to the Allium test. Seeds of onion (Allium cepa) were incubated on Petri dishes. When the roots of germinating onion reached 1 cm length, they were transferred to Petri dishes containing aqueous solutions of the test compounds wherein germanium concentrations were 0.0625%, 0.125%, 0.25%, and 0.5%. The results clearly demonstrated that the germanium compounds have a cytostatic effect, which is associated with a decrease in the mitotic cycle. The germanium compound with aspartic acid was tested in six in-hospital patients who were diagnosed as having oval cancer and malignant tumors of the uterus. The patients received orally 100 mg of the substance in the form of a 10% solution twice daily. The tumors were removed surgically. All patients showed a noticeable improvement in health. In addition, five patients did not show exudate either in the abdominal cavity, or in the internal pelvic cavity. Small exudate was found only in one patient. There were no toxic side effects. None patients showed infiltration in post-operational examination carried out one month later.

The method disclosed in the patent DE 3212817 has the following drawbacks:

Not only does the use of potassium and sodium hydroxides for transferring germanium dioxide into a soluble form through the formation of potassium or sodium salts of metagermanic acid complicate the process, but this is also responsible for the occurrence of alkali-metal cations in the final products, and this can be undesired in the pharmaceutical use of the resulting compounds;

Germanium complex compounds with acids are frequently stable only in aqueous solution and are destroyed in an attempt at being isolated from water; in the patent DE 3212817, a germanium compound with succinic acid is isolated only in Example 1; the other examples produce solutions of germanium with aspartic and carboxylic acids, and this may serve as evidence of their instability in a solid form and the impossibility of being isolated from aqueous solution;

In view of the fact that the final products obtained in Examples 2 to 4 are solutions, the resulting aqueous solutions containing organogermanium compounds are mixtures comprising potassium or sodium salts of metagermanic acid, carboxylic acids, and germanium compounds with carboxylic acids; medical uses of such an aqueous solution that contains the target product is difficult because of the occurrence therein of the aforementioned contaminants;

The preparation of organogermanium compounds with amino acids is exhausted by the use of aspartic acid (see Example 3)

OBJECTIVES OF THE INVENTION

One objective of the present invention consists in the development of a simple method for the preparation of germanium complex compounds with chemically different amino acids and carboxylic acids such that would be stable and easily transferable into aqueous solution.

Another objective of the invention consists in the development of a method for the preparation of germanium complex compounds with amino acids and carboxylic acids such that would provide controlling the ratio of germanium to the amino acid and carboxylic acid in the complex compound and controlling the composition of the complex.

One more objective of the invention consists in the provision of germanium complex compounds with chemically different amino acids and carboxylic acids such that would be stable and easily transferable into aqueous solution.

Still one more objective of the invention consists in the provision of germanium complex compounds having a desired composition and a desired ratio of germanium to the amino acid and carboxylic acid in the complex.

SUMMARY OF THE INVENTION

The claimed objectives are achieved due to the claimed method for the preparation of germanium complex compounds with amino acids and carboxylic acids, the method comprising: mixing germanium dioxide with water thereby obtaining an aqueous suspension of germanium dioxide; adding to the resulting germanium dioxide suspension of at least one amino acid or a mixture of at least one amino acid and at least one carboxylic acid; heating the resulting mixture at a temperature between 40 and 100° C. for 2 to 14 hours in order to produce a target product, which is a germanium complex compound with the amino acid or with the amino acid and carboxylic acid; and removing water to obtain a powdery product.

The thus-produced germanium complex compounds with amino acids or with amino acids and carboxylic acids are white amorphous powders, well soluble in water, which have the general structural formula $$Ge[OH]_a[AA]_b[CA]_b \qquad (I)$$

wherein AA is an amino acid selected from a large number of known α-amino acids such as (but not limited to) alanine, aminobutyric acid, arginine, aspartic acid, valine, norvaline, histidine, glycine, glutamic acid, isoleucine, leucine, norleucine, lysine, methionine, ornithine, serine, tyrosine, threonine, tryptophan, and phenylalanine; and/or from other amino acids such as γ-aminobutyric acid;

CA is a carboxylic acid selected from monocarboxylic acids such as (but not limited to) acetic acid, dichloroacetic acid, and isovaleric acid; dicarboxylic acids such as (but not limited to) azelaic acid, malonic acid, oxalic acid, phthalic acid, and succinic acid; hydroxycarboxylic acids such as (but not limited to) tartaric acid, citric acid, lactic acid, and malic acid; hydroxy-benzoic acids such as (but not limited to) salicylic acid; and pyridine monocarboxylic acids such as (but not limited to) nicotinic acid; and a=0÷3, b=1÷3, c=0÷3, wherein 1≤b+c≤4;

and wherein all AAs in the complex compound are the same or different and all CAs in the complex compound are the same or different.

THE DETAILED DISCLOSURE OF THE INVENTION

The invention proposes a simple method, comprising a minimal number of steps, for the preparation of stable germanium complex compounds with a wide range of amino acids and carboxylic acids, such that could easily be isolated as powder and re-transferred into aqueous solution by being dissolved in water. The method provides germanium complex compounds with diverse ratios of germanium to amino acids and carboxylic acids. The compounds are free of undesired ions and are suitable for use in pharmaceutical agents.

The method of the invention is characterized by mixing germanium dioxide with water to obtain an aqueous suspension, adding an amino acid or an amino acid and a carboxylic to the aqueous suspension of germanium dioxide under stirring, stirring the mixture at a temperature of between 40 and 100° C. for 2 to 14 hours to obtain a solution of the target product, and then removing the water to obtain the target product as an amorphous white powder.

The germanium dioxide used can be either the α polymorph, which is water insoluble, or the β polymorph, which is water soluble. More preferred is water-insoluble α-germanium dioxide, which yields, when mixed with water, a suspension of germanium dioxide in water.

Several amino acids and several carboxylic acids can be added according to this method.

The amino acids (AAs) useful in the method of the invention include amino acids from a wide range of known α-amino acids such as (but not limited to) alanine, aminobutyric acid, arginine, aspartic acid, valine, norvaline, histidine, glycine, glutamic acid, isoleucine, leucine, norleucine, lysine, methionine, ornithine, serine, tyrosine, threonine, tryptophan, phenylalanine; and from other amino acids such as γ-aminobutyric acid. A mixture of different amino acids, in particular, mixtures of the above-listed amino acids, can also be used. α-Amino acids are preferably useful in the context of the method.

The carboxylic acids (CAs) useful in the method of the invention include monocarboxylic acids, dicarboxylic acids, hydroxycarboxylic acids, hydroxybenzoic acids, or mixtures of these acids. The useful monocarboxylic acids include (but are not limited to) acetic acid, dichloroacetic acid, and isovaleric acid. The useful dicarboxylic acids include (but are not limited to) azelaic acid, malonic acid, oxalic acid, phthalic acid, and succinic acid. The useful hydroxycarboxylic acids include (but are not limited to) tartaric acid, citric acid, lactic acid, and malic acid. The useful hydroxybenzoic acids include (but are not limited to) salicylic acid. The useful pyridine monocarboxylic acids include (but are not limited to) nicotinic acid.

The ratio between germanium and acids in a germanium complex compound depends on the amounts of the amino acid and carboxylic acids that are added to the aqueous suspension of germanium dioxide. Controlling the ratio between the amount of the acid added and germanium dioxide, one can obtain complex compounds with different ratios between the acid and germanium dioxide. When the acid is mixed with germanium dioxide in the stoichiometric proportion, the complex compound is formed wherein the molar ratio of germanium to the acid is 1:1. When the acid is added in a twofold, threefold, or fourfold amount relative to the stoichiometry, the resulting complex compound has the acid to germanium molar ratio of 2:1, 3:1, or 4:1, respectively.

The term "acid" in the context of this application means an amino acid or a mixture of amino acids, a carboxylic acid or a mixture of carboxylic acids, or the total of an amino acid and a carboxylic acid.

The temperatures at which the reaction is carried out to produce the target germanium complex compound with amino acids and carboxylic acids are between 40 and 100° C. Preferred temperatures are between 80 and 100° C., and more preferred temperatures are between 85 and 100° C.

The reaction time is from 2 to 14 hours. Preferred reaction times are between 4 and 10 hours, and still more preferred reaction times are between 4 and 6 hours.

The formation of germanium-containing complex compounds is signified by the complete dissolution of germanium dioxide (when insoluble germanium dioxide is used) and the formation of a clear solution. Other methods can also be used for monitoring product formation, for example those involving sampling and analyzing samples.

In order to isolate germanium-containing compounds, the solution is filtered and then water is removed from the solution by some known method. Any of the known methods is suitable for this purpose, for example water evaporation, vacuum distillation, or lyophilization (freeze-drying).

Different amino acids and carboxylic acids can be added to an aqueous suspension of germanium dioxide simultaneously as a mixture of acids, or otherwise consecutive addition of different amino acids and carboxylic acids can be used.

One variant of the method is a method wherein amino acids are added to an aqueous suspension of germanium dioxide, the resulting mixture is heated under stirring at a temperature of between 80 and 100° C. for a period of between 5 and 10 hours until a clear solution is formed, and then a carboxylic acid is added and heating at 80-100° C. is continued for 1-2 hours, the solution is filtered, and the water is removed to obtain a complex compound in solid form.

Another variant of the method is a method wherein a carboxylic acid is added to an aqueous suspension of germanium dioxide, the resulting mixture is heated under stirring at a temperature of between 80 and 100° C. for a period of between 5 and 10 hours until a clear solution is formed, then amino acid is added, and heating at 80-100° C. is continued for 1-2 hours, the solution is filtered, and the water is removed to obtain a complex compound in solid form.

One more variant of the method is a method wherein a mixture of an amino acid and a carboxylic acid is added to an aqueous suspension of germanium dioxide, the resulting mixture is heated under stirring at a temperature of between 80 and 100° C. for a period of between 2 and 10 hours until a clear solution is formed, the solution is filtered, and the water is removed to obtain a complex compound in solid form.

The product is obtained as a white amorphous powder which is readily soluble in water.

NMR and IR spectra were studied for various germanium complex compounds with amino acids and carboxylic acids produced by the method according to the invention, and elemental analysis has been performed for these complex compounds. The data thus obtained indicate that these germanium-containing compounds have a general structural formula:

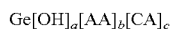  (I)

wherein AA is an amino acid selected from a large number of known α-amino acids such as (but not limited to) alanine, aminobutyric acid, arginine, aspartic acid, valine, norvaline, histidine, glycine, glutamic acid, isoleucine, leucine, nor-leucine, lysine, methionine, ornithine, serine, tyrosine, threonine, tryptophan, and phenylalanine; and/or from other amino acids such as γ-aminobutyric acid;

CA is a carboxylic acid selected from monocarboxylic acids such as (but not limited to) acetic acid, dichloroacetic acid, and isovaleric acid; dicarboxylic acids such as (but not limited to), azelaic acid, malonic acid, oxalic acid, phthalic acid, and succinic acid; hydroxycarboxylic acids such as (but not limited to) tartaric acid, citric acid, lactic acid, and malic acid; hydroxybenzoic acids such as (but not limited to) salicylic acid; and pyridine monocarboxylic acids such as (but not limited to nicotinic acid; and $a=0\div 3$, $b=1\div 3$, $c=0\div 3$, wherein $1 \leq b+c \leq 4$.

The aforementioned acids in aqueous solution form complex compounds with germanium dioxide, which are not only stable in aqueous solution but can also be isolated in a pure form. This is enhanced by the formation of a coordination bond between nitrogen and germanium atoms (N→Ge) or between the OH oxygen of the hydroxycarboxylic acid and germanium (HO→Ge).

The particular structural formulas of preferred compounds II-XI produced according to the invention are given below.

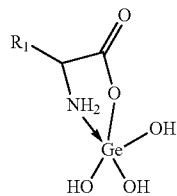

II

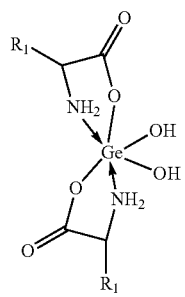

III

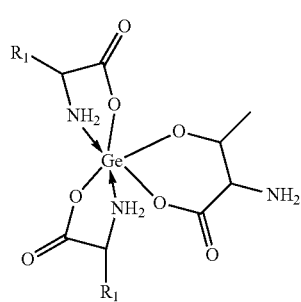

IV

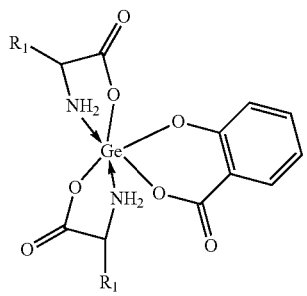

V

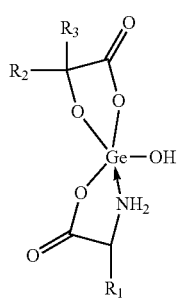

VI

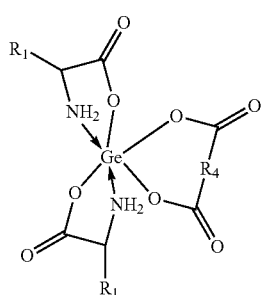

VII

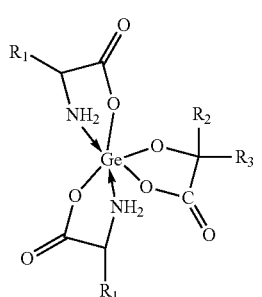

VIII

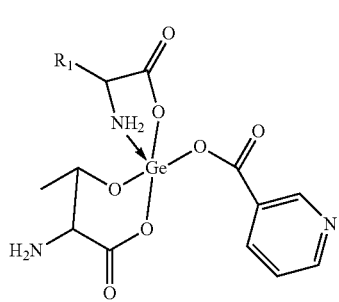

IX

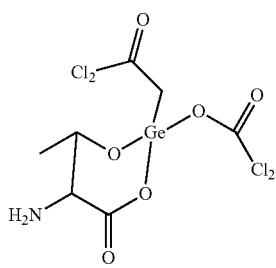

X

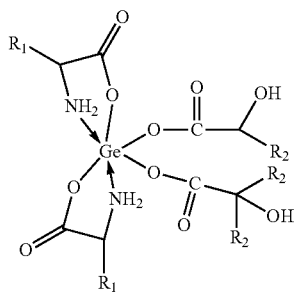

XI

Herein $R_1$ represents the corresponding α-amino acid moiety; $R_2$ and $R_3$ represent the corresponding hydroxycarboxylic acid moieties; and $R_4$ represents the corresponding dicarboxylic acid moieties.

All of the compounds from II to XI are covered by the general structural formula (I). For example, compounds II to IV are germanium complex compounds with α-amino acids, wherein the molar ratio of the amino acid to germanium (index (b) in the structural formula (I)) is 1, 2, and 3, respectively, and wherein the ratio of the number of OH groups to germanium (index (a) in the structural formula (I)) is 3, 2, and 0, respectively. Compounds V and VIII are each a germanium complex compound with two α-amino acid molecules and one α-hydroxycarboxylic acid molecule (in the structural formula (I): b=2, c=1, and a=0); compound VI is a germanium complex compound with one α-amino acid molecule and one α-hydroxycarboxylic acid molecule (b=1, c=1, and a=1); compound VII is a germanium complex compound with two α-amino acid molecules and one dicarboxylic acid molecule (b=2, c=1, and a=0), etc.

The presence of an amino acid and a carboxylic acid in germanium-containing compounds endows the complex compounds with high biological activity, so that these complex compounds can be used as active components in the design and production of new agents for use in medicine, pharmaceutics, and veterinary, for example for diagnosing, preventing, and treating various diseases in humans and animals, and in the production of diverse cosmetic products. The preferred germanium complex compounds as claimed should be expected to exhibit the same type of biological activity as the acids involved therein, and this is just demonstrated by Example 15. However, a germanium complex compound can also exhibit another type of biological activity such that is not intrinsic to the acids involved therein. The high biological activities of medicines wherein the active components are germanium complex compounds of the invention are due to the high solubilities of these compounds and the involvement therein of biologically active germanium and biologically active acids.

Changing the nature of the amino acid and/or of the carboxylic acid used, one can obtain germanium complex compounds that would have very high biological activities to serve as the basis for the manufacture of highly efficient agents and medicaments suitable both for pharmaceutical and for medicinal, cosmetic, and veterinary uses. These may be pharmaceutical compositions comprising germanium complex compounds of the invention and optionally conventional pharmaceutically acceptable excipients, drugs, or pharmaceuticals embodied in diverse dosage forms (as solutions, tablets, ointments, gels, and so on); or cosmetic compositions embodied as, for example, creams, gels, and so on.

The claimed invention will further be illustrated by examples, which are intended only to illustrate, but in no way to limit, the invention.

EXAMPLE 1

Into a round-bottomed flask equipped with a stirrer and a thermometer, charged are 3.12 g (0.03 mol) α-germanium dioxide $GeO_2$, 5.22 g (0.03 mol) arginine $HN=C(NH_2)NH(CH_2)_3CH(NH_2)COOH$, and 150 mL distilled water. The suspension is stirred under heating (at 85-95° C.) for 2 hours. The resulting clear solution is cooled and filtered, and the water is removed on a rotary evaporator. The product is obtained as 8.4 g (94%) of a white amorphous powder. IR and NMR spectra for the product compound are shown in FIGS. 1a and 1b. Elemental analysis data are displayed in Table 1. The elemental analysis and spectroscopic data show that the product corresponds to compound (II).

EXAMPLE 2

Into a round-bottomed flask equipped with a stirrer and a thermometer, charged are 3.12 g (0.03 mol) α-germanium dioxide $GeO_2$, 9.84 g (0.06 mol) lysine monohydrate $H_2N(CH_2)_4CH(NH_2)COOH.H_2O$, and 200 mL distilled water. The suspension is stirred under heating (at 85-95° C.) for 2 hours until a clear solution is formed. Then, the solution is cooled and filtered, and the water is removed on a rotary evaporator. The product is obtained as 11.4 g (96%) of a white amorphous powder. IR and NMR spectra for the product compound are shown in FIGS. 2a and 2b. Elemental analysis data are displayed in Table 1. The elemental analysis and spectroscopic data show that the product corresponds to compound (III).

EXAMPLE 3

Into a round-bottomed flask equipped with a stirrer and a thermometer, charged are 3.12 g (0.03 mol) α-germanium dioxide $GeO_2$, 10.71 g (0.09 mol) threonine $CH_3CH(OH)CH(NH_2)COOH$, and 300 mL distilled water. The suspension is stirred under heating (at 90-100° C.) for 2 hours until a clear solution is formed. Then, the solution is cooled and filtered, and the water is removed on a rotary evaporator. The product is obtained as 12.4 g (97%) of a white amorphous powder. IR and NMR spectra for the product compound are shown in FIGS. 3a and 3b. Elemental analysis data are displayed in Table 1. The elemental analysis and spectroscopic data show that the product corresponds to compound (IV).

EXAMPLE 4

Into a round-bottomed flask equipped with a stirrer and a thermometer, charged are 3.12 g (0.03 mol) α-germanium dioxide $GeO_2$, 10.44 g (0.06 mol) arginine $HN=C(NH_2)NH(CH_2)_3CH(NH_2)COOH$, and 300 mL distilled water. The suspension is stirred under heating (at 85-95° C.) for 1 hour until a clear solution is formed. Then added is 5.64 g (0.03 mol) azelaic acid HOOC(CH$_2$)$_7$COOH, and stirring is continued for 2 hours. Then, the solution is cooled and filtered, and the water is removed on a rotary evaporator. The product is obtained as 17.2 g (95%) of a white amorphous powder. IR and NMR spectra for the product compound are shown in FIGS. 4a and 4b. Elemental analysis data are displayed in Table 1. The elemental analysis and spectroscopic data show that the product corresponds to compound (VII).

EXAMPLE 5

Into a round-bottomed flask equipped with a stirrer and a thermometer, charged are 3.12 g (0.03 mol) α-germanium dioxide GeO$_2$, 4.92 g (0.03 mol) lysine monohydrate H$_2$N (CH$_2$)$_4$CH(NH$_2$)COOH.H$_2$O, and 150 mL distilled water. The suspension is stirred under heating (at 85-95° C.) for 1 hour until a clear solution is formed, and then added is 6.3 g (0.03 mol) citric acid monohydrate (HOOCCH$_2$)$_2$C(OH) COOH.H$_2$O. After stirring for 1 hour, the solution is cooled and filtered, and the water is removed on a rotary evaporator. The product is obtained as 12.2 g (96%) of a white amorphous powder. IR and NMR spectra for the product compound are shown in FIGS. 5a and 5b. Elemental analysis data are displayed in Table 1. The elemental analysis and spectroscopic data show that the product corresponds to compound (VI).

EXAMPLE 6

Into a round-bottomed flask equipped with a stirrer and a thermometer, charged are 3.12 g (0.03 mol) α-germanium dioxide GeO$_2$, 4.5 g (0.06 mol) glycine H$_2$NCH$_2$COOH, 6.3 g (0.03 mol) citric acid monohydrate (HOOCCH$_2$)$_2$C(OH) COOH.H$_2$O, and 350 mL distilled water. The suspension is stirred under heating (at 90-100° C.) for 4 hours. The resulting clear solution is cooled and filtered, and the water is removed on a rotary evaporator. The product is obtained as 11.7 g (95%) of a white amorphous powder. IR and NMR spectra for the product compound are shown in FIGS. 6a and 6b. Elemental analysis data are displayed in Table 1. The elemental analysis and spectroscopic data show that the product corresponds to compound (VIII).

EXAMPLE 7

Into a round-bottomed flask equipped with a stirrer and a thermometer, charged are 3.12 g (0.03 mol) α-germanium dioxide GeO$_2$, 8.82 g (0.06 mol) glutamic acid HOOC (CH$_2$)$_2$ CH(NH$_2$)COOH, 4.02 g (0.03 mol) malic acid HOOCCH(OH)CH$_2$COOH, and 350 mL distilled water. The suspension is stirred under heating (at 85-100° C.) for 3 hours. The resulting clear solution is cooled and filtered, and the water is removed on a rotary evaporator. The product is obtained as 14.0 g (94%) of a white amorphous powder. IR and NMR spectra for the product compound are shown in FIGS. 7a and 7b. Elemental analysis data are displayed in Table 1. The elemental analysis and spectroscopic data show that the product corresponds to compound (VIII).

EXAMPLE 8

Into a round-bottomed flask equipped with a stirrer and a thermometer, charged are 3.12 g (0.03 mol) α-germanium dioxide GeO$_2$, 7.14 g (0.06 mol) threonine CH$_3$CH(OH)CH (NH$_2$)COOH, 3.48 g (0.03 mol) fumaric acid, HOOCCH=CHCOOH, and 350 mL distilled water. The suspension is stirred under heating (at 85-100° C.) for 5 hours. The resulting clear solution is cooled and filtered, and the water is removed on a rotary evaporator. The product is obtained as 11.8 g (93%) of a white amorphous powder. IR and NMR spectra for the product compound are shown in FIGS. 8a and 8b. Elemental analysis data are displayed in Table 1. The elemental analysis and spectroscopic data show that the product corresponds to compound (VII).

EXAMPLE 9

Into a round-bottomed flask equipped with a stirrer and a thermometer, charged are 3.12 g (0.03 mol) α-germanium dioxide GeO$_2$, 9.84 g (0.06 mol) lysine monohydrate H$_2$N (CH$_2$)$_4$CH(NH$_2$)COOH.H$_2$O, 4.14 g (0.03 mol) salicylic acid HOC$_6$H$_4$COOH, and 300 mL distilled water. The suspension is stirred under heating (at 85-100° C.) for 5 hours. The resulting clear solution is cooled and filtered, and the water is removed on a rotary evaporator. The product is obtained as 14.1 g (94%) of a white amorphous powder. IR and NMR spectra for the product compound are shown in FIGS. 9a and 9b. Elemental analysis data are displayed in Table 1. The elemental analysis and spectroscopic data show that the product corresponds to compound (V).

EXAMPLE 10

Into a round-bottomed flask equipped with a stirrer and a thermometer, charged are 3.12 g (0.03 mol) α-germanium dioxide GeO$_2$, 5.22 g (0.03 mol) arginine HN=C(NH$_2$)NH (CH$_2$)$_3$CH(NH$_2$)COOH, 3.48 g (0.03 mol) fumaric acid HOOCCH=CHCOOH, and 300 mL distilled water. The suspension is stirred under heating (at 80-90° C.) for 4 hours. The resulting clear solution is cooled and filtered, and the water is removed on a rotary evaporator. The product is obtained as 15.2 g (95%) of a white amorphous powder. IR and NMR spectra for the product compound are shown in FIGS. 10a and 10b. Elemental analysis data are displayed in Table 1. The elemental analysis and spectroscopic data show that the product corresponds to compound (VII).

EXAMPLE 11

Into a round-bottomed flask equipped with a stirrer and a thermometer, charged are 3.12 g (0.03 mol) α-germanium dioxide GeO$_2$, 7.14 g (0.06 mol) threonine CH$_3$CH(OH)CH (NH$_2$)COOH, 3.69 g (0.03 mol) nicotinic acid NC$_5$H$_4$COOH, and 350 mL distilled water. The suspension is stirred under heating (at 85-100° C.) for 5 hours. The resulting clear solution is cooled and filtered, and the water is removed on a rotary evaporator. The product is obtained as 12.0 g (93%) of a white amorphous powder. IR and NMR spectra for the product compound are shown in FIGS. 11a and 11b. Elemental analysis data are displayed in Table 1. The elemental analysis and spectroscopic data show that the product corresponds to compound (IX).

EXAMPLE 12

Into a round-bottomed flask equipped with a stirrer and a thermometer, charged are 3.12 g (0.03 mol) α-germanium dioxide GeO$_2$, 7.74 g (0.06 mol) dichloroacetic acid Cl$_2$CHCOOH, and 250 mL distilled water. The suspension is stirred under heating (at 85-100° C.) for 4-5 hours. To the resulting clear solution, added is 3.57 g (0.03 mol) threonine CH$_3$CH(OH)CH(NH$_2$)COOH. The solution is stirred under heating (at 85-100° C.) for 2 hours. Then, the solution is cooled and filtered, and the water is removed by lyophilization (freeze drying). The product is obtained as 12.8 g (96%) of a white amorphous powder. Elemental analysis data are displayed in Table 1 (compound X).

EXAMPLE 13

Into a round-bottomed flask equipped with a stirrer and a thermometer, charged are 3.12 g (0.03 mol) α-germanium dioxide $GeO_2$, 6.3 g (0.03 mol) citric acid monohydrate $(HOOCCH2)_2C(OH)COOH.H_2O$, 4.02 g (0.03 mol) malic acid $HOOCCH(OH)CH_2COOH$, 4.5 g (0.06 mol) glycine $H_2NCH_2COOH$, and 350 mL distilled water. The suspension is stirred under heating (at 90-100° C.) for 4 hours. The resulting clear solution is cooled and filtered, and the water is removed on a rotary evaporator. The product is obtained as 15.5 g (95%) of a white amorphous powder. Elemental analysis data are displayed in Table 1 (compound XI).

according to the Russian State Standard (GOST) 12.1.007-76 or as Class V toxicity (practically nontoxic) according to the Hodge and Sterner scale (1943).

EXAMPLE 15

Biological Activity Study of the Germanium Complex Compound with Arginine and Azelaic Acid Prepared as in Example 4

Some properties of the germanium complex compound with arginine and azelaic acid prepared as in Example 4 were studied.

The room-temperature water solubility of this complex compound was greater than 10% against the value of 0.2% for the solubility of the precursor azelaic acid. A 1% solution had pH of 5.4.

The $LD_{50}$ value for the studied compound was greater than 5 000 mg/kg, and thereby it can be classified as Class

TABLE 1

Elemental analysis data for produced compounds

| Example | Compound | $R_1$-$R_4$ | Found, % | | | | Bulk formula | MM | Calculated, % | | | |
|---|---|---|---|---|---|---|---|---|---|---|---|---|
| | | | C | H | Ge | N | | | C | H | Ge | N |
| 1 | II | $R_1$: —$C_3H_6NH(C=NH)NH_2$ | 24.55 | 5.48 | 24.81 | 19.14 | $C_6H_{16}GeN_4O_5$ | 296.8 | 24.28 | 5.43 | 24.46 | 18.88 |
| 2 | III | $R_1$: —$C_4H_8NH_2$ | 36.52 | 7.17 | 18.56 | 14.02 | $C_{12}H_{28}GeN_4O_6$ | 397.0 | 36.30 | 7.11 | 18.29 | 14.11 |
| 3 | IV | $R_1$: —$CH(OH)CH_3$ | 34.03 | 5.51 | 17.23 | 9.76 | $C_{12}H_{23}GeN_3O_9$ | 425.9 | 33.84 | 5.44 | 17.05 | 9.87 |
| 4 | VII | $R_1$: —$C_3H_6NH(C=NH)NH_2$, $R_4$: —$(CH_2)_7$ | 41.55 | 6.72 | 12.09 | 18.44 | $C_{21}H_{40}GeN_8O_8$ | 605.2 | 41.67 | 6.66 | 12.00 | 18.52 |
| 5 | VI | $R_1$: —$C_4H_8NH_2$, $R_{2,3}$: —$CH_2COOH$ | 33.75 | 4.82 | 17.21 | 6.48 | $C_{12}H_{20}GeN_2O_{10}$ | 424.9 | 33.92 | 4.74 | 17.09 | 6.59 |
| 6 | VIII | $R_1$: —H, $R_{2,3}$: —$CH_2COOH$ | 29.39 | 3.48 | 17.56 | 6.75 | $C_{10}H_{14}GeN_2O_{11}$ | 410.8 | 29.24 | 3.43 | 17.67 | 6.82 |
| 7 | VIII | $R_1$: —$C_2H_4COOH$, $R_2$: —H, $R_3$: —$CH_2COOH$ | 33.71 | 4.13 | 14.78 | 5.57 | $C_{14}H_{20}GeN_2O_{13}$ | 496.9 | 33.84 | 4.06 | 14.61 | 5.64 |
| 8 | VII | $R_1$: —$CH(OH)CH_3$, $R_4$: —$CH=CH$ | 34.23 | 4.36 | 17.31 | 6.52 | $C_{12}H_{18}GeN_2O_{10}$ | 422.9 | 34.08 | 4.29 | 17.17 | 6.62 |
| 9 | V | $R_1$: —$C_4H_8NH_2$ | 45.58 | 6.15 | 14.69 | 11.08 | $C_{19}H_{30}GeN_4O_7$ | 499.1 | 45.72 | 6.06 | 14.55 | 11.23 |
| 10 | VII | $R_1$: —$C_3H_6NH(C=NH)NH_2$, $R_4$: —$CH=CH$ | 36.24 | 5.33 | 13.57 | 20.84 | $C_{16}H_{28}GeN_8O_8$ | 533.0 | 36.05 | 5.29 | 13.62 | 21.02 |
| 11 | IX | $R_1$: —$CH(OH)CH_3$ | 39.31 | 4.50 | 16.78 | 9.66 | $C_{14}H_{19}GeN_3O_8$ | 429.9 | 39.11 | 4.45 | 16.89 | 9.77 |
| 12 | X | — | 21.43 | 2.15 | 16.08 | 3.27 | $C_8H_9GeCl_4NO_7$ | 445.6 | 21.56 | 2.02 | 16.29 | 3.14 |
| 13 | XI | $R_1$: —H, $R_2$: —$CH_2COOH$ | 30.69 | 3.82 | 13.45 | 5.11 | $C_{14}H_{20}GeN_2O_{16}$ | 544.9 | 30.86 | 3.70 | 13.32 | 5.14 |

Determination of Biological Activity of the Produced Complex Compounds

EXAMPLE 14

Acute Toxicity

Acute toxicity was determined in nonlinear white male mice with body weights of 18-20 g with one-time intragastric (i/g) administration in doses of 1 000, 2 000, 3 000, 4 000, and 5 000 mg/kg of a 20% aqueous solutions in an amount of 0.1, 0.2, 0.3, 0.4, and 0.5 mL per 20 g mouse body weight, respectively. Each of the compounds prepared in Examples 1 to 13 was administered individually.

No signatures of intoxication, a lag in body weight gain, or death of animals were found in 14 days after administering each of the compounds.

No violations in the movements, reflexes, or behavior of animals were observed over the range of the doses studied. Anatomical studies have not found any change in the lungs, kidneys, spleen, or other organs.

The $LD_{50}$ values in mice for the compounds studied were greater than 5 000 mg/kg, and thereby these compounds can be classified as Class IV hazard in terms of the hazard classification of substances by their impact on the body IV hazard in terms of the hazard classification of substances by their impact on the body according to the Russian State Standard (GOST) 12.1.007-76 or as Class V toxicity (practically nontoxic) according to the Hodge and Sterner scale (1943). Toxicological and hygienic studies discovered no skin-irritating, skin-resorptive, or sensitizing action of the new compound.

When this compound was administered to nonlinear mice for 14 days intragastrically in a dose of 1 000 mg/kg, the animals of the experimental group showed no reliable changes in the body weight or the weight coefficients of parenchymatous organs (liver, kidneys, and spleen) compared to the respective values in control group animals.

The specific biological activity of the germanium complex compound with arginine and azelaic acid prepared as in Example 4 against a number of microorganisms was studied in experiments using serial dilutions in agar and diffusion into agar.

Dosage forms of the product according to the invention were prepared as creams and gels which comprised, respectively, 3% and 5% the germanium complex compound with arginine and azelaic acid produced as in Example 4.

The references used were samples of the commercial product Skinoren (manufactured by Intendis Manufacturing SpA, Italy) in cream (containing 20% azelaic acid) and gel (containing 15% azelaic acid) dosage forms.

The germanium complex compound with arginine and azelaic acid was shown to be active against a range of microorganisms, in particular against *Propionibacterium* acnes. *Staphylococcus aureus* (including methicillin-resistant strains (MRSA)), *S. Epidermidis, Candida albicans*, and others. The results of comparative tests are compiled below in Tables 2 and 3.

TABLE 2

Results of comparative antibacterial activity tests for dosage forms comprising a germanium complex compound with azelaic acid and arginine and the commercial product Skinoren

| Tested microorganisms | Minimal inhibitory concentration (MIC), mkg/mL | | | |
|---|---|---|---|---|
| | the product according to the invention (comprising the compound of Example 4) | | Skinoren | |
| | 3% cream | 3% gel | 20% cream | 15% gel |
| 1 | 2 | 3 | 4 | 5 |
| *Staphylococcus aureus*, methicillin-sensitive | | | | |
| S. aureus 151010 | 1.5 | 12.5 | 0.75 | 12.5 |
| S. aureus 151021 | 1.5 | 12.5 | 0.75 | 12.5 |
| *Staphylococcus aureus*, methicillin-resistant | | | | |
| S. aureus 18 | 1.5 | 12.5 | 0.75 | 12.5 |
| S. aureus 81 | 1.5 | 12.5 | 0.75 | 12.5 |
| S. epidermidis 20638 | 0.75 | 0.75 | 0.75 | 0.75 |
| S. epidermidis 21457 | 0.75 | 1.5 | 0.75 | 0.75 |
| Candida albicans ATCC 24433 | 0.75 | 1.5 | 1.5 | 1.5 |

From the data displayed in Table 2, one can see that the germanium complex compound with azelaic acid and arginine has biological activity against a range of microorganisms. Differences between the MIC values for the Skinoren samples and the dosage forms prepared using the germanium complex compound produced as in Example 4, do not exceed 1-2-fold dilution, which corresponds with the experimental error. With this, the concentration of the active substance in the dosage forms comprising the germanium complex compound is five to six times lower than in the Skinoren samples. Thus, the activity of the germanium complex compound with azelaic acid and arginine against the microorganisms indicated in Table 2 is higher than the respective activity of azelaic acid.

Biological activity values against *Propionibacterium* acnes for the germanium complex compound produced as in Example 4 are given below. The references used were samples comprising azelaic acid which are known to be active against *Propionibacterium* acnes.

All samples tested in this experiment were studied with 1:5 dilution. The results of comparative tests are displayed in Table 3.

TABLE 3

Results of comparative antibacterial activity tests against *Propionibacterium acnes* for dosage forms comprising the germanium complex compound with azelaic acid and arginine and the commercial product Skinoren

| Tested microorganisms | Size of zones where the growth of tested microorganisms is inhibited (mm) in the presence of | | | | | |
|---|---|---|---|---|---|---|
| | Skinoren | | the product according to the invention (comprising the compound of Example 4) | | | |
| | 15% gel | 20% cream | 3% gel | 5% gel | 3% cream | 5% cream |
| 1 | 2 | 3 | 4 | 5 | 6 | 7 |
| *Propionibacterium acnes* 5592 | 12.5 | 15.5 | 17.5 | 22 | 18.5 | 27 |
| *Propionibacterium acnes* A-1 | 15.5 | 15 | 25 | 17 | 24 | 30 |

As one can see from the results of the experiment displayed in Table 3, the zones where the growth of tested microorganisms is inhibited in the presence of the 3 and 5% dosage forms according to the invention that comprised the compound of Example 4, exceed the growth inhibition zones that appeared under the action of Skinoren 15% gel or Skinoren 20% cream.

The final dose of the active substance (taking into account the fivefold dilution of the products) for Skinoren samples was 3% for Skinoren 15% gel and 4% for Skinoren 20% cream; the *Propionibacterium* acnes growth inhibition zones for these products were 12.5 to 15.5 mm and 15.5 to 15 mm, respectively.

For the 3% gel and 3% cream products according to the invention comprising the complex as produced in Example 4, the final dose of the active substance was 0.6% (taking into account the fivefold dilution). The *Propionibacterium* acnes growth inhibition zones for these products were 17.5 to 25 mm and 18.5 to 24 mm, respectively.

For the 5% gel and cream products according to the invention, the final dose of the active substance was 1% (taking into account the fivefold dilution). The *Propionibacterium* acnes growth inhibition zones for these products were 22-17 mm and 27-30 mm, respectively.

Thus, the germanium complex compound with arginine and azelaic acid produced as in Example 4 in cream and gel dosage forms in concentrations of 3 and 5% has the activity against *Propionibacterium* acnes that considerably exceeds the activity of the commercial products Skinoren 15% gel and Skinoren 20%) cream.

One factor that is likely to be responsible for the high activity against *Propionibacterium* acnes of the products of the invention comprising the complex compound prepared according to Example 4, is the higher water solubility (10%) of the complex compound produced as in Example 4 compared to the water solubility of ordinary azelaic acid (0.2%). The high activity of the complex compound according to the invention will allow using lower working concentrations of the claimed germanium complex compound for treating diseases which are caused by, in particular, *Propionibacterium* acnes. This will allow avoiding some side effects caused by high concentrations of azelaic acid, such as skin irritation, redness, burning sensation, and others.

INDUSTRIAL APPLICABILITY

The presence of an amino acid and a carboxylic acid in germanium-containing compounds endows them with high biological activity, and they can be useful for the design and preparation of new pharmaceuticals.

The prepared complex compounds are nontoxic and can also find application as new agents in healthcare and medicine and in medical, pharmaceutical, veterinary, biotechnology, cosmetics and perfumes, and food industries.

The invention claimed is:
1. A germanium complex compound of the general formula

$$Ge[OH]_a[AA]_b[CA]_c \qquad (I)$$

wherein AA is an amino acid,
CA is a carboxylic acid,
a=0-3, b=1-3 and c=1-3, and 1≤b+c≤4,
wherein all AAs in the complex compound are the same or different, and
all CAs in the complex compound are the same or different;
wherein the amino acids are α-amino acids;
wherein the carboxylic acids are selected from the group consisting of acetic acid, dichloroacetic acid, isovaleric acid, azelaic acid, malonic acid, oxalic acid, phthalic acid, fumaric acid, succinic acid, tartaric acid, citric acid, lactic acid, malic acid, hydroxybenzoic acid and pyridine monocarboxylic acid; and
wherein the germanium complex compound has any one of the structural formulas V to XI:

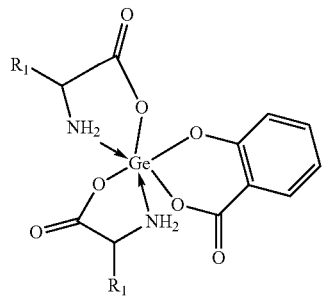
V

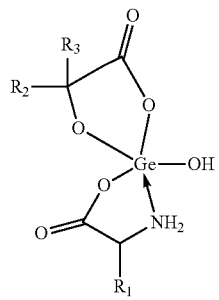
VI

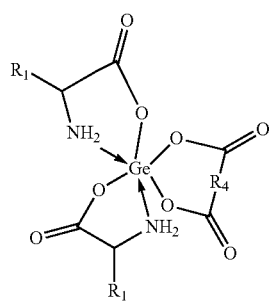
VII

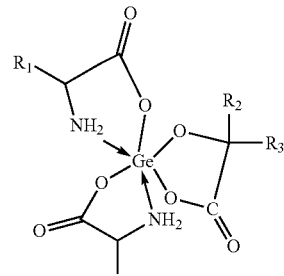
VIII

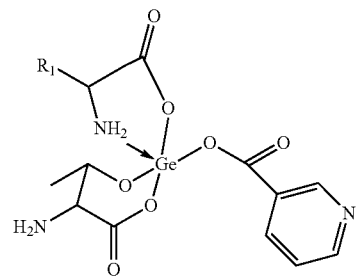
IX

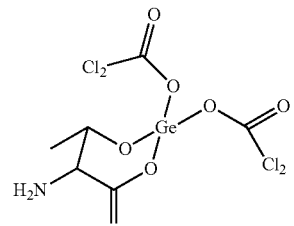
X

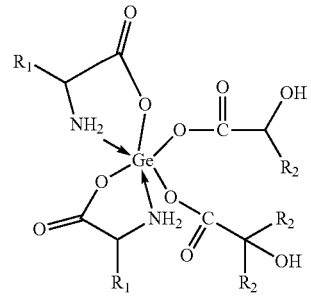
XI wherein $R_1$ represents an α-amino acid moiety; $R_2$ and $R_3$ represent hydroxycarboxy acid moieties; and $R_4$ represents dicarboxylic acid moieties.

2. The germanium complex compound according to claim 1, wherein the amino acids are selected from the group consisting of alanine, aminobutyric acid, arginine, aspartic acid, valine, norvaline, histidine, glycine, glutamic acid, isoleucine, leucine, norleucine, lysine, methionine, ornithine, serine, tyrosine, threonine, tryptophan, and phenylalanine.

3. The germanium complex compound according to claim 1 having:
structural formula VII, wherein the amino acid is arginine or threonine, and the carboxylic acid is azelaic acid or fumaric acid; or
structural formula VI, wherein the amino acid is lysine, and the carboxylic acid is citric acid; or
structural formula VIII, wherein the amino acid is glycine or glutamic acid, and the carboxylic acid is citric acid or malic acid; or structural formula V, wherein the amino acid is lysine, and the carboxylic acid is salicylic acid; or structural formula IX, wherein the amino acid is threonine, and the carboxylic acid is nicotinic acid; or structural formula X, wherein the carboxylic acid is dichloroacetic acid, and the amino acid is threonine; or structural formula XI, wherein the amino acid is glycine, and the carboxylic acid is citric acid and malic acid.

4. The germanium complex compound according to claim 1, wherein the amino acid is arginine and the carboxylic acid is azelaic acid.

5. A method for preparing the germanium complex compound according to claim 1 comprising:
providing an aqueous suspension of α-germanium dioxide;
adding to the aqueous suspension of α-germanium dioxide at least one amino acid and at least one carboxylic acid;
heating the resulting mixture under stirring at a temperature of between 40 and 100° C. for 2-14 hours, followed by filtering and removing water to isolate a complex compound from the aqueous solution.

6. The method according to claim 5, wherein the heating is carried out at a temperature of between 80 and 100° C. for 4-10 hours.

7. The method according to claim 6, wherein the heating is carried out at a temperature of between 85 and 100° C. for 4-6 hours.

8. The method according to claim 5, wherein the heating under stirring is carried out until a clear solution is formed.

9. The method according to claim 5, wherein the amino acids and the carboxylic acids are added consecutively or as a mixture.

10. The method according to claim 9, wherein an amino acid is added to the aqueous suspension of α-germanium dioxide, the resulting mixture is heated under stirring at a temperature of between 80 and 100° C. for 5-10 hours until a clear solution is formed, then a carboxylic acid is added and the heating is continued at 80-100° C. for 1-2 hours, the solution is filtered, and the water is removed to obtain a complex compound in a solid form.

11. The method according to claim 9, wherein a carboxylic acid is added to the aqueous suspension of α-germanium dioxide, the resulting mixture is heated under stirring at a temperature of between 80 and 100° C. for 5-10 hours until a clear solution is formed, then an amino acid is added and the heating is continued at 80-100° C. for 1-2 hours, the solution is filtered, and the water is removed to obtain a complex compound in a solid form.

12. The method according to claim 9, wherein a mixture of an amino acid and a carboxylic acid is added to the aqueous suspension of a-germanium dioxide, the resulting mixture is heated under stirring at a temperature of between 80 and 100° C. for 2-10 hours until a clear solution is formed, the solution is filtered, and the water is removed to obtain a complex compound in a solid form.

13. The method according to claim 5, wherein the water is removed by a method selected from the group consisting of evaporation, vacuum distillation under heating, and lyophilization (freeze drying).

14. A pharmaceutical composition or a medicament comprising, as an active component, the germanium complex compound according to claim 1.

15. The pharmaceutical composition or a medicament comprising, as an active component, the germanium complex compound according to claim 4.

16. The pharmaceutical composition or a medicament according to claim 15 suitable for treating diseases caused by *Propionibacterium* acnes.

* * * * *